United States Patent
Forbes et al.

(10) Patent No.: US 10,973,794 B2
(45) Date of Patent: Apr. 13, 2021

(54) DENTAL COMPOSITION AND USE

(71) Applicant: CALSCIENCE INTERNATIONAL LTD., Lothian (GB)

(72) Inventors: Iain William George Forbes, Lothian (GB); William Forbes, Lothian (GB)

(73) Assignee: CALSCIENCE INTERNATIONAL LTD., Lothian (GB)

( * ) Notice: Subject to any disclaimer, the term of this patent is extended or adjusted under 35 U.S.C. 154(b) by 0 days.

(21) Appl. No.: 15/550,388

(22) PCT Filed: Feb. 10, 2016

(86) PCT No.: PCT/GB2016/050316
§ 371 (c)(1),
(2) Date: Aug. 11, 2017

(87) PCT Pub. No.: WO2016/128745
PCT Pub. Date: Aug. 18, 2016

(65) Prior Publication Data
US 2018/0028481 A1      Feb. 1, 2018

(30) Foreign Application Priority Data
Feb. 11, 2015   (GB) ............................. 1502268

(51) Int. Cl.
*A61K 31/216*   (2006.01)
*A61Q 11/00*    (2006.01)
*A61K 8/37*     (2006.01)

(52) U.S. Cl.
CPC ............. *A61K 31/216* (2013.01); *A61K 8/37* (2013.01); *A61Q 11/00* (2013.01); *A61K 2800/782* (2013.01)

(58) Field of Classification Search
CPC .................................................... A61K 31/216
See application file for complete search history.

(56) References Cited

U.S. PATENT DOCUMENTS

| | | | |
|---|---|---|---|
| 5,395,624 | A | 3/1995 | Li et al. |
| 7,968,129 | B2 | 6/2011 | Golz-Berner et al. |
| 9,486,400 | B2 | 11/2016 | Osborne et al. |
| 2002/0037827 | A1 | 3/2002 | Wang et al. |
| 2003/0166567 | A1 | 9/2003 | Quirk et al. |
| 2004/0029945 | A1 | 2/2004 | O'Brien et al. |

(Continued)

FOREIGN PATENT DOCUMENTS

| | | |
|---|---|---|
| CN | 1381236 A | 11/2002 |
| CN | 1839815 A | 10/2006 |

(Continued)

OTHER PUBLICATIONS

Miyamae et al., Bioorg. Med. Chem., 2012;20:5844-5849.*

(Continued)

*Primary Examiner* — San Ming R Hui
(74) *Attorney, Agent, or Firm* — ALGM LLP; Harry J. Guttman

(57) ABSTRACT

Use of a composition for the prevention, amelioration and/or treatment of conditions, disorders and/or diseases associated with senescence and/or inflammation of the teeth and/or associated structures and tissues in the mouth, the composition comprising a conjugate of quinic acid with at least one molecule of caffeic acid, or a derivative, isomer or salt thereof.

20 Claims, 6 Drawing Sheets

(56) References Cited

U.S. PATENT DOCUMENTS

| | | |
|---|---|---|
| 2004/0034098 A1 | 2/2004 | Varani et al. |
| 2004/0044000 A1 | 3/2004 | Bunker et al. |
| 2004/0105897 A1 | 6/2004 | Monroe et al. |
| 2004/0116491 A1 | 6/2004 | King et al. |
| 2004/0127420 A1 | 7/2004 | Quirk |
| 2004/0142950 A1 | 7/2004 | Bunker et al. |
| 2004/0167120 A1 | 8/2004 | Klingler et al. |
| 2004/0175349 A1 | 9/2004 | Tsuji et al. |
| 2004/0176393 A1 | 9/2004 | Newton et al. |
| 2006/0074108 A1 | 4/2006 | Gupta |
| 2008/0063693 A1* | 3/2008 | Cook ............... A01N 25/10 424/443 |

FOREIGN PATENT DOCUMENTS

| | | |
|---|---|---|
| CN | 101057678 A | 10/2007 |
| CN | 102266318 A | 12/2011 |
| EP | 0577516 A1 | 1/1994 |
| EP | 1283037 A1 | 2/2003 |
| EP | 2324840 A1 | 5/2011 |
| JP | 2006-213636 A | 8/2006 |
| JP | 2010-120908 A | 6/2010 |
| WO | 02/47703 A2 | 6/2002 |
| WO | 2006/127525 A2 | 11/2006 |
| WO | 2015/044649 A1 | 4/2015 |

OTHER PUBLICATIONS

Battagim et al., Journal of Enzyme Inhibition and Medicinal Chemistry, 2012; 27(2): 232-240 (Year: 2012).*

PCT/GB2016/050316 ISR mailed May 11, 2016, 3 pages.

PCT/GB2016/050316 Written Opinion dated May 11, 2016, 4 pages.

Agren, "Matrix metalloproteinases (MMPs) are required for re-epithelialization of cutaneous wounds" Arch. Dermatol. Res. (1999) vol. 291, pp. 583-590.

Ashworth et al, "Fibrillin degradation by matrix metalloproteinases: implications for connective tissue remodeling" Biochem Journal (1999) vol. 340, pp. 171-181.

Bellizzi et al., "A novel VNTR enhancer within the SIRT3 gene, a human homologue of SIR2, is associated with survival at oldest ages" Genomics (2005) vol. 85, pp. 258-263.

Bolognia, "Dermatologic and cosmetic concerns of the older woman" Clin Geniatr Med (1993) vol. 9, No. 1, pp. 209-229.

Browner et al., "Matrilysin—Inhibitor Complexes: Common Themes among Metalloproteases" Biochemistry (1995) vol. 34, pp. 6602-6610.

Inoue et al., "SIRT2, a tubulin deacetylase, acts to block the entry to chromosome condensation in response to mitotic stress" Oncogene (2007) vol. 26, pp. 945-957.

Jacobson et al., "Skin changes with aging and disease" Wound Repair Regen. (1996) vol. 4, No. 3, pp. 311-315.

Moses et al., "Temporal Study of the Activity of Matrix Metalloproteinases and Their Endogenous Inhibitors During Wound Healing" J Cell Biochem. (1996) vol. 60, pp. 379-386.

North et al, "The Human Sir2 Ortholog, SIRT2, Is an NAD-Dependent Tubulin Deacetylase" Mol Cell (2003) vol. 11, pp. 437-444.

Saarialho-Kere "Patterns of matrix metalloproteinase and TIMP expression in chronic ulcers" Arch. Dermatol. Res. (1998) vol. 290 (Suppl), pp. S47-S54.

Scher et al., "SirT3 is a nuclear NAD+-dependent histone deacetylase that translocates to the mitochondria upon cellular stress" Genes Dev (2007) vol. 21, pp. 920-928.

Skjot-Arkil el al., "Measurement of MMP-9 and -12 degraded elastin (ELM) provides unique information on lung tissue degradation" BMC Pulmonary Medicine (2012) vol. 12, Article 34. (12 pages).

Uitto et al., "Proteolytic host cell enzymes in gingival crevice fluid" Periodontology 2000 (2003) vol. 31, pp. 77-104.

Vaalamo et al., "Patterns of matrix metalloproteinase and TIMP-1 expression in chronic and normally hearing human cutaneous wounds" Brit. J. Dermatol. (1996) vol. 135, No. 1, pp. 52-59.

Wada et al., "Phenoxyphenyl Sulfone N-Formylhydroxylamines (Retrohydroxamates) as Potent, Selective, Orally Bioavailable Matrix Metalloproteinase Inhibitors" J Med. Chem (2002) vol. 45, No. 1, pp. 219-232.

International Search Report for Application No. PCT/GB20141052863 dated Mar. 19, 2015, 9 pages.

U.S. Appl. No. 15/025,105 Restriction Requirement dated Jun. 23, 2017, 7 pages.

U.S. Appl. No. 15/025,105 Response to Restriction Requirement dated Nov. 22, 2017, 13 pages.

U.S. Appl. No. 15/025,105 nonfinal Office action dated Apr. 20, 2018, 50 pages.

U.S. Appl. No. 15/025,105 Response to nonfinal Office action dated Sep. 20, 2018, 14 pages.

U.S. Appl. No. 15/025,105 final Office action dated Apr. 19, 2019, 28 pages.

U.S. Appl. No. 15/025,105 RCE Response to final Office action dated Oct. 18, 2019, 14 pages.

Antognoni, Fabiana et al., "Irbic Acid, a Dicaffeoylquinic Acid Derivative from Cell Cultures", Fitoterapia, vol. 82, No. 7, 2011, pp. 950-954.

Cheng et al, "Interaction of Sirt3 With OGG1 Contributes to Repair of Mitochondrial DNA and Protects From Apoptotic Cell eath Under Oxidative Stress," Cell Death dis, 2013, vol. 4, article e731. (11 pages).

Dai et al., "P16ink4a Can Initiate an Autonomous Senescence Program," Oncogene 2000, 19: pages. 1613-1622.

De Fijter, J.W., "Increased Immunogenicity and Cause of Graft Loss of Old Donor Kidneys," J Am Soc Nephrol 2001, 12: pages. 1538-1546.

Donev et al. "Neuronal Death in Alzheimer's Disease and Therapeutic Opportunities," J Cell Mol Med 2009; 13: pages. 4329-4348.

Facino et al., "Echinacoside and Caffeoyl Conjugates Protect Collage from Free-Radical-Induced Degradation: A potential use of Echinacea Extracts in the Prevention of Skin Photodamage" 1995, Planta Med, vol. 61, pp. 510-514 (Year: 1995).

Figueroa et al, "Presenilin-Dependent Gamma-Secretase Activity Modulates Neurite Outgrowth," Neurobiology of Disease, 2002; vol. 9, pp. 49-60.

Gongora, Luis et al., "Effects of Caffeoyl Conjugates of Isoprenyl-Hydroquinone Glucoside and Quinic Acid on Leukocyte Function", Life Sciences, vol. 71, No. 25, Nov. 1, 2002, pp. 2995-3004.

Han, J. et al., "Neuroprotective Effect of 3,5-di-0-Caffeoylquinic Acid on SH-SY5Y Cells and Senescence-Accelerated-Prone Mice 8 Through the Up-Regulation of Phosphoglycerate Kinase-1" Neuroscience, vol. 169, No. 3, 2010, pp. 1039-1045.

Hwang, Y.P. et al., "3-Caffeoyl, 4-Dihydrocaffeoylquinic Acid from Salicornia Hergacea Inhibits Tumor Cell Invasion by Regulating Protein Kinase C-Delta-Dependent Matrix Matalloproteinase-9 Expression", Toxicology Letters, Elsevier Biomedical Press, Amsterdam, NL, vol. 198, No. 2, Oct. 5, 2010, pp. 200-209.

Joosten, Sa et al; "Telomere Shortening and Cellular Senescence in a Model of Chronic Renal Allograft Rejection," Amer J Pathol, 2003, 162(4): pp. 1305-1312.

Kong et al, "Sirtuin 3, a New Target of PGC-1a, Plays an Important Role in the Suppression of ROS and Mitochondrial Biogenesis," PLoS One, 2010: 5(7): Article e11707. (13 pages).

Linskens, MH et al., "Cataloging Altered Gene Expression in Young and Senescent Cells Using Enhanced Differential Display," Nucleic Acids Res 1995, 23: 3244-3251.

Liu et al, "Cataloging Altered Gene Expression in Young and Senescent Cells Using Enhanced Differential Display," J Biol. Chem., 2012; 287: pp. 32307-32311.

Lorenzl, Stefan et al., "Matrix Metalloproteinase-9 Is Elevated in 1-Methyl-4-Phenyl-1,2,3.6-Tetrahydropyridine-Induced Parkinsonism in Mice", NeuroMolecular Medicine, Human Press, Inc., vol. 5, 2004, pp. 119-131.

Melk, Anette et al., "Telomere Shortening in Kidneys with Age", J. Am. Soc. Nephrol., vol. 11, 2000, pp. 444-453.

(56) References Cited

OTHER PUBLICATIONS

Melk, Anette et al., "Cell Senescence and Its Implications for Nephrology", J. Am. Soc. Nephrol., vol. 12, 2001, pp. 385-393.

Melk, Anette et al., "Increased Expression of Senescence-Associated Cell Cycle Inhibitor P16INK4a in Deteriorating Renal Transplants and Diseased Native Kidney", American Journal of Transplantation, vol. 5, 2005, pp. 1375-1382.

Miyamae, Yusaku et al., "3,4,5-tri-o-caffeoylquinic Acid Inhibits Amyloid Beta-Mediated Cellular Toxicity on Sh-Sy5Y Cells Through the Upregulation of PGAM1 and G3PDH", Cytotechnology, vol.63, No. 2, Mar. 2011, pp. 191-200.

Outeiro, Tiago Fleming et al., "Sirtuin 2 Inhibitors Rescue a-Synuclein-Mediated Toxicity in Models of Parkinson's Disease", Science, vol. 317, Jul. 27, 2007, pp. 516-519.

Paul, LC., "Chronic Renal Transplant Loss", Perspectives in Clinical Nephrology, Kidney International, vol. 47, 1995, pp. 1491-1499.

Puangpraphant, Sirima et al., "Dicaffeoylquinic Acids in Yerba Mate {Ilex paraguariensis St. Hilare) ilhibit NF-kappa]B Nucleus Translocation in Macrophases and Induce Apoptosis by Activating Caspases-8 and -3 in Human colon Cancer Cells", Molecular Nutrition & Food Research, vol. 55, No. 10, Oct. 8, 2011, pp. 1509-1522.

Serrano, Manuel et al., "Putting the Stress on Senescence", Current Opinion in Cell Biology, vol. 13, 2001, pp. 748-753.

Sherr, Charles J_ et al., "Cdk Inhibitors: Postive and Negative Regulators of G1-Phase Progression", Genes & Development, vol. 13, 1999, pp. 1501-1512.

Stein, Gretchen et al., "Differential Roles for Cyclin-Dependent Kinase Inhibitors p21 and p16 in the Mechanisms of Senescence and Differentiation in Human Fibroblasts", Molecular and Cellular Biology, Mar. 1999, vol. 19, pp. 2109-2117.

Database WPI, Week 200720, Thomson Scientific, London GB, AN 2007-193035, XP0027237090. (2 pages).

Database WPI, Week, 200361, Thomson Scientific, London, GB; AN 2003-637335, XP002737091. (1 page).

Database WPI, Week 201043, Thomson Scientific, London, GB; AN 2010-G03107, XP00273092. (3 pages).

Database WPI, Thomson Scientific, London, GB; AN 2011-Q85864, XP002737093. (3 pages).

Database WPI, Week 200660, Thomson Scientific, London, GB; An 2006-582266, XP002737094. (3 pages).

Database WPI, Week 200822, Thomson Scientific, London GB, AN 2008-D0339, XP002734649. (2 pages).

English language abstract and machine-assisted English translation for CN 1381236 extracted from espacenet.com database on May 15, 2017, 12 pages.

English language abstract and machine-assisted English translation for CN 1839815 extracted from espacenet.com database on May 15, 2017, 33 pages.

English language abstract and machine-assisted English translation for CN 101057678 extracted from espacenet.com database on May 15, 2017, 31 pages.

English language abstract and machine-assisted English translation for CN 102266318 extracted from espacenet.com database on May 15, 2017, 16 pages.

English language abstract for EP 0 577 516 extracted from espacenet.com database on May 15, 2017, 2 pages.

English language abstract and machine-assisted English translation for JP 2006-213636 extracted from espacenet.com database on May 15, 2017, 19 pages.

English language abstract and machine-assisted English translation for JP 2010-120908 extracted from espacenet.com database on May 15, 2017, 26 pages.

U.S. Appl. No. 15/025,105 nonfinal Office action dated Sep. 22, 2020, 36 pages.

* cited by examiner

DENTAL COMPOSITION AND USE

CROSS-REFERENCE TO RELATED APPLICATIONS

This application is a U.S. National Stage Entry of International Application No. PCT/GB2016/050316 filed Feb. 10, 2016, entitled "DENTAL COMPOSITION AND USE" which is herein incorporated by reference in its entirety, and which claims priority to GB 1502268.4 filed Feb. 11, 2015, entitled "DENTAL COMPOSITION AND USE" which is herein incorporated by reference in its entirety.

The invention relates to the use of a composition for the prevention, amelioration and/or treatment of conditions associated with the process of senescence and/or inflammation in the mouth.

The term senescence, including cellular senescence, involves perceptible changes in cells such as the shortening of telomeres, double-strand DNA breaks and an increase in the levels of p16 INK4a. The process of senescence may be natural, premature, induced or accelerated. Induced or accelerated senescence has been found to be involved in a number of conditions and diseases associated with the mouth, and has been shown to occur in transplanted cells, tissues and organs. Examples of natural senescence processes that occur in the mouth include the loss of teeth and gum retraction.

Sirtuins (SIRTs) are mammalian homologues of the Silent Information Regulator (Sir2) protein found in yeast and are enzymes of class III histone deacetylases (HDACs). Class III HDACs induce transcriptional repression and gene silencing by removal of acetyl groups from histones and regulate gene expression in response to changes in redox and cell metabolism. The Sirtuin 2 (Sir2) family depends on the compound nicotinamide adenine dinucleotide ($NAD^+$) for subsequent reactions, converting acetyl lysine in the presence of $NAD^+$ to O-acetyl-ADP-ribose and nicotinamide. Regulated by the ratio of $NAD^+$ to NADH, the activity of sirtuins varies not only with metabolic changes that occur within the cell but also with feedback inhibition that occurs in response to the level of generated nicotinamide.

Seven members of the sirtuin family have been found in mammals and are typically numbered SIRT1 to SIRT7. SIRT1 is mainly localised in the nucleus and has complex roles in cell senescence and tumour suppression by limiting DNA damage by reactive oxygen species and genomic instability. The latter is the subject of current research on cancer cells. SIRT2 is a deacetylase present in the cytosol and is mainly found co-localised with tubulin which it deacetylates (North, B. J., et al., Mol Cell, 2003, 11(2), 437-44; Inoue, T., et al., Oncogene 2007, 26(7), 945-57). SIRT2 functions as a regulator of mitotic progression and hence the over expression of SIRT2 has been found to delay cell cycle progression. SIRT2 is typically ubiquinated and degraded via the 26s proteasome mechanism. SIRT3 is found in the nucleus and in mitochondria and exerts its function as a deacetylase only after cleavage of its signal peptide. It has been found that SIRT3 expression may be enhanced due to a polymorphism and that the allele lacking this activity is also absent in males over 90 years of age (Bellizzi, D. et al., Genomics, 2005, 85(2), 258-63). This may link the insufficiency of SIRT3 to the process of senescence. SIRT3 is primarily a nuclear enzyme, but is localised to the mitochondria when the cell is stressed or when over expression of the enzyme occurs (Scher, M. B., et al., Genes Dev (2007) 21(8), 920-28). Of the remaining sirtuins, SIRT4 has been shown to lack deacetylase activity and is found with SIRT5 in mitochondria. The latter has not as yet been shown to have a precise biological function and is a deacetylase. SIRT6 is located in the nucleus and may be involved in promoting resistance to DNA damage and base pair excision repair. SIRT7 is found in the nucleolus. Depletion of SIRT7 arrests cell proliferation and triggers apoptosis.

The matrix metalloproteinases (MMPs) are part of the family of endopeptidases (proteolytic enzymes) and are distinguished by having a zinc atom associated with three cysteine residues, together with a methionine residue. More than thirty MMPs are present in mammals and are numbered accordingly, for example, MMP-1 (collagenase 1), MMP-2 (gelatinase A) and MMP-9 (gelatinase B). The MMPs are known to hydrolyse large proteins in the connective tissue, degrade large proteins of the extracellular matrix and basal sheets (for example, collagens, gelatins, elastins, proteoglycans and fibronectins) and are expressed at very low levels under normal conditions of organ growth, tissue renewal and regeneration. Under certain conditions in mammals, over expression of MMPs, and in particular MMP-9, may result in disorganization and/or destruction of the extracellular matrix and/or the spread of cancer. The MMPs are induced by pro-inflammatory cytokines such as tumour necrosis factor-alpha (TNF-alpha) and interleukin-1 beta (IL-1 beta).

The MMPs are also involved in activating other MMPs and are necessary in the biosynthesis of the key pro-inflammatory cytokine, TNF-alpha. This cytokine can influence the activation of other pro-inflammatory cytokines such as interleukin-1 beta (IL-1 beta) and is of significance in up regulating nuclear factor-kappaB (NF-kappaB). The latter in turn is able to activate MMP-9, therefore creating a self-perpetuating stimulatory pro-inflammatory loop. TNF-alpha is of relevance in a wide range of clinical conditions and diseases and its over expression may be a key contributory factor in several disorders. In addition, TNF-alpha may contribute significantly to downstream effects or events within the cell.

An over-activity of an MMP, or an imbalance between an MMP and the corresponding natural tissue inhibitor of matrix metalloproteinase (TIMP) is associated with the destruction or breakdown of the extracellular matrix in cells and may therefore result in tissue damage, disease or the extension of disease. Whilst certain MMPs are required for normal embryological development, these enzymes are known to appear and disappear over a specific timeframe and within a range of concentration. Some conditions and diseases in the mouth that involve over expression of MMP-9 include, for example, demineralization of tooth enamel, breakdown of dentin matrix in carious lesions, gum retraction and inflammatory diseases of the mouth.

A number of small non-peptide molecules have been demonstrated to inhibit MMP-9, but so far, these have been of relatively low potency. These molecules include antibiotics such as minocycline, doxycycline and erythromycin. Other low to medium inhibitors of MMP-9 are: arginine, nicotinamide, vitamin D3 and curcumin (from the spice turmeric). However, none of these compounds has been shown to have anti-senescence properties. Efforts have been made to identify highly selective MMP inhibitors having little or no side effects. These highly selective inhibitors of MMPs, particularly inhibitors of MMP-9, have not previously been shown to have an inhibitory effect on cell senescence. The authors of U.S. 2004/0034098 suggest that senescence of human skin can be delayed with the topical application of an MMP inhibitor, preferably a retinoid (which indirectly inhibits MMP). In U.S. 2004/0127420 and U.S. 2003/0166567, the authors refer to peptide inhibitors of MMPs for treating wounds. These inhibitors have sequences that are related to the cleavage regions of pro-enzyme forms of MMP.

It is known that MMP-9 is a collagenase and increases the degradation of elastin, gelatine types I and V, collagen type IV and V and fibrillin. Inhibition of MMP-9 advantageously reduces or prevents the breakdown of these components and thus helps to maintain or improve elasticity or firmness (Bolognia, Clin Geniatr Med 1993 (9): 209-229; Skjøt-Arkil et al, BMC Pulmonary Medicine 2012 (12): 34; Ashworth et al, Biochem Journal 1999 (340, Part 1): 171-181).

Some publications which refer to inhibition of the MMPs are: Wadda et al., J Med. Chem, 45, 219-232; U.S. 2002/0037827; U.S. 2004/0029945; U.S. 2004/0175349; U.S. 2004/0176393; U.S. 2004/0167120; U.S. 2004/0142950; U.S. 2004/0044000; U.S. 2004/0116491 and U.S. 2004/0105897.

The following publications refer to conditions and disorders which may benefit from MMP inhibition: U.S. 2006/0074108; U.S. 2004/0034098; U.S. 2004/0127420; U.S. 2003/0166567; Agren, M. S., Arch. Dermatol. Res., 1999, 291583-291590; Browner, M. F. et al., Biochemistry, 1995, 34, 6602-6610; Moses, M. A. et al., J Cell Biochem., 60, 379; Saarialho and Kere, UK Arch. Dermatol. Res., 1998, 290 (Suppl), 47-54; Vaalamo, M. et al., 1996, Brit. J. Dermatol., 135, 52-59. Although these publications suggest a biological role for these compounds, the precise cellular pathways have not been demonstrated.

The present invention seeks to provide a composition for use in preventing, ameliorating and/or treating conditions associated with the processes of senescence and/or inflammation of the mouth.

According to the invention, there is provided use of a composition for the prevention, amelioration and/or treatment of conditions, disorders and/or diseases associated with senescence and/or inflammation of the teeth and/or associated structures and tissues in the mouth, the composition comprising a conjugate of quinic acid with at least one molecule of caffeic acid, or a derivative, isomer or salt thereof.

In a preferred embodiment, the conjugate is represented by the following formula (I):

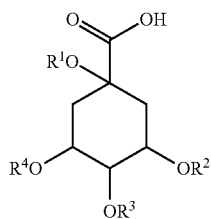

I wherein at least one of $R^1$, $R^2$, $R^3$ or $R^4$ is a hydrogen atom; and wherein at least one of $R^1$, $R^2$, $R^3$ or $R^4$ that is not hydrogen is a caffeoyl group, represented by the following formula (II):

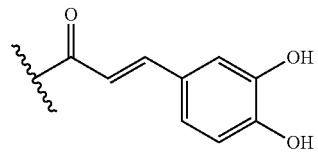

II or a derivative, isomer or salt thereof.

Within the context of the invention, conjugate means a compound formed by joining at least two individual moieties. Preferably, the conjugate is an ester of caffeic acid and quinic acid.

Preferably, in the formation of the conjugate, the hydrogen of $OR^1$, $OR^2$, $OR^3$ and/or $OR^4$ reacts with the carboxylic acid functional group of caffeic acid to form an ester.

By way of example, a typical reaction that may occur to form a conjugate within the context of the invention is shown below:

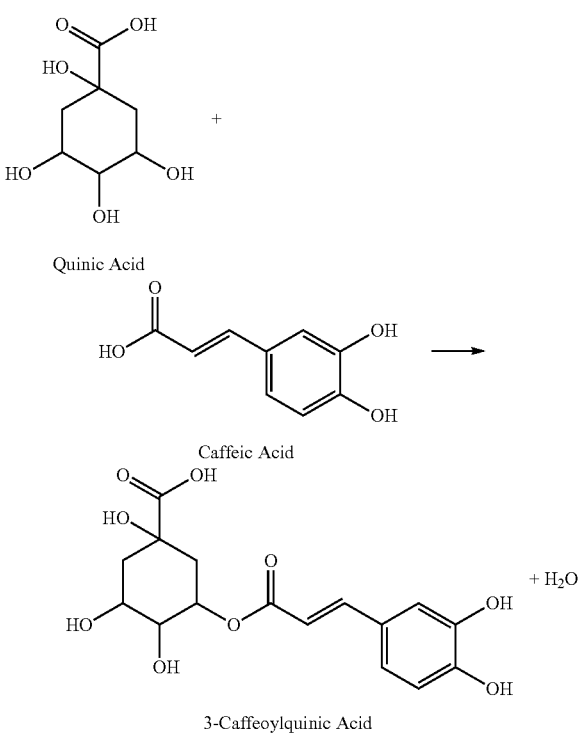

The above example shows the formation of 3-caffeoylquinic acid. The invention is not limited to use of a composition comprising this conjugate and other conjugates may be used in accordance with the present invention.

Preferably, the composition comprises a dicaffeoylquinic acid and/or a tricaffeoylquinic acid, or a derivative, isomer or salt thereof.

Preferably, the conjugate is selected from 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, 4,5-dicaffeoylquinic acid, or 3,4,5-tricaffeoylquinic acid, or a derivative, isomer or salt thereof.

The nomenclature of the dicaffeoylquinic or tricaffeoylquinic acids may be represented, for example, as 1,3-O-dicaffeoylquinic acid or 3,4,5-O-tricaffeoylquinic acid, etc.

Preferably, the use of the composition inhibits one or more of the matrix metalloproteinases (MMPs), nuclear factor kappa B (NF-kappa B), cytokines and/or tissue inhibitors of matrix metalloproteinase (TIMP) activators.

Preferably, there is provided use of the composition for the prevention, amelioration and/or treatment of disorders and/or diseases associated with an increase in the expression of one or more MMP genes and/or proteins.

In a preferred embodiment, the use of the composition inhibits the activity of MMP-9 and/or MMP-2. MMP-9 is a collagenase and is associated with the degradation of several components such as elastin, gelatine types I and V, collagen type IV and V and fibrillin, which may decrease the elasticity and firmness of the tissues of the mouth. Inhibition of MMP-9 therefore prevents the breakdown of these components and improves properties, such as elasticity and firmness.

Advantageously, the composition may be used to inhibit analogues, orthologues, homologues, derivatives and variants of MMPs, preferably MMP-9. MMP-9 typically comprises a functional metal cation in the catalytic active site and is capable of hydrolysing polypeptides. Advantageously, the composition may inhibit full-length mammalian MMPs, or truncated forms of MMPs, or a catalytic domain from these enzymes which comprises a metal cation.

Preferably, there is provided use of the composition for the prevention, amelioration and/or treatment of disorders and/or diseases associated with an increase in the expression of MMP-9 and/or MMP-2.

Advantageously, use of the composition may enhance extracellular matrix cohesion, preferably of the teeth and associated structures and tissues of the mouth. Advantageously, the use of the composition may stimulate the biosynthesis of fibrillar collagens, elastin and/or fibrillins. Advantageously, the use of the composition may inhibit breakdown of elastin and/or collagenase type IV.

Preferably, use of the composition controls the concentration of matrix metalloproteinases (MMPs) in saliva. In this embodiment, the composition affects the salivary glands and associated tissues of the mouth. It is preferred that the use of the composition controls the concentration of MMP-9 in saliva.

Typically, use of the composition is associated with a decrease in the expression of the sirtuin 2 gene or protein, and/or an increase in expression of the sirtuin 3 gene or protein.

Advantageously, use of the composition activates the expression of the sirtuin 3 gene to enhance the production of the sirtuin 3 protein. Advantageously, the composition is capable of inhibiting the expression of the sirtuin 2 gene to inhibit the production of the sirtuin 2 protein. A reduced level of SIRT3 in cells and tissues is thought to be a possible marker of senescence. Advantageously, use of the composition may inhibit the up regulation of SIRT2.

Advantageously, the composition is capable of inhibiting the expression of the p16INK4a gene (a biomarker of cell senescence) in cells, tissues or organs, for example, following oxidant challenge.

Preferably, use of the composition may inhibit key pro-inflammatory cytokines, for example, interleukin-1 beta (IL-1 beta), interleukin-6 (IL-6), tumour necrosis factor alpha (TNF-alpha), the chemokine interleukin-8 (CXCL-8; IL-8) and interferon-gamma (IFN-gamma) in cells tissues or organs. These are the downstream effects of inhibiting Pp ser 536 of NF-kappaB.

In one embodiment, use of the composition may modulate expression of the Human Protection of Telomeres 1 (hPOT1) gene. Such modulation indicates a significant protective effect on telomeres which under normal circumstances shorten with oxidant challenge and cell senescence.

Advantageously, the composition may be used to inhibit MMPs, NF-kappa B and senescence-associated genes.

Preferably, there is provided use of a composition for the prevention, amelioration and/or treatment of demineralisation of teeth and/or associated structures in the mouth. In one embodiment, there may be provided use of a composition for the prevention, amelioration and/or treatment of demineralisation of the enamel and/or dentine of the teeth.

Preferably, there is provided use of a composition for the stimulation and/or promotion of remineralisation of teeth and/or associated structures in the mouth following demineralisation. In one embodiment, there may be provided use of a composition for the stimulation and/promotion of remineralisation of the enamel and/or dentine of the teeth.

Advantageously, the composition decreases the concentration of MMPs such as MMP-9 in the mouth.

Preferably, there is provided use of a composition for the prevention, amelioration and/or treatment of leukoplakia.

Preferably, there is provided use of a composition for the prevention, amelioration and/or treatment of chronic inflammatory disease of the teeth and associated structures of the mouth.

In one embodiment, there may be provided use of a composition for the prevention, amelioration and/or treatment of conditions of the teeth and/or associated structures of the mouth associated with senescence.

Preferably, there is provided use of a composition for the prevention, amelioration and/or treatment of tissue shrinkage or contraction that may occur following application of a dental implant or prosthesis in the mouth.

Preferably, there is provided use of a composition for incorporation into a coating or other material used in a dental implant or prosthesis.

Preferably, there is provided use of a composition for the prevention, amelioration and/or treatment of dental caries. Advantageously, use of the composition may prevent, ameliorate and/or treat carious lesions of the teeth.

In one embodiment, the composition may be applied to the teeth to improve the cosmetic appearance thereof.

Preferably, there is provided use of a composition for incorporation into teeth whitening agents. In this embodiment, there is provided use of the composition for the prevention, amelioration and/or treatment of conditions affected by compounds such as hydrogen peroxide and/or associated derivatives which may be generated by the use of such agents. In this embodiment, the free radicals generated may lead to up regulation of NF-kappaB, proinflammatory cytokines and MMPs, in particular, MMP-9. These processes may then cause initiation of demineralisation and/or erosion of the teeth, in particular the enamel of the teeth.

In one embodiment, the conjugate may be extracted from a natural source. Preferably, the conjugate is a plant extract, preferably an artichoke extract. In another embodiment, the conjugate may be synthesised or genetically engineered from plants, bacteria, fungi, mould, algae or another suitable source. Preferably, the composition comprises a plant extract.

In one embodiment, the conjugate may further comprise a lipid, fatty acid, alcohol or sugar attachment to another dicaffeoylquinic acid or tricaffeoylquinic acid, or a derivative, isomer or salt thereof.

Preferably, the conjugate may comprise at least one acceptable carrier and may be carried within a vesicle, micelle, liposome, nanoparticle or other suitable vehicle.

In one embodiment, the composition may be directly applied to the teeth or associated structures in the mouth, for example, by a dental practitioner during a surgical procedure, or by injection.

In another embodiment, the composition may be applied topically to the teeth and/or associated structures. Typically, the patient may topically apply the composition to the teeth and associated structures of the mouth to prevent demineralisation of the teeth and/or to prevent or reduce the formation of caries and/or to prevent or reduce decay of the teeth. Preferably, the composition may be topically applied in the form of a mouthwash, paste such as toothpaste, lotion, gel, powder or other suitable medium.

In one embodiment, the composition may be administered via a delivery system which may comprise vitamins, hormones, minerals, plant extracts, concentrates of plant extracts, anti-inflammatory agents, anti-oxidants, penetration enhancers, solublizers, and/or pH adjusters.

In one embodiment, the composition may be administered by a parenteral route. In alternative embodiments, the composition may be administered by a transdermal, subcutaneous, intravenous, oral, sublingual, lingual route, or by inhalation or instillation.

In another embodiment, the composition may be administered by incorporation into an implant including a dental implant, plate or other structure, or by use of a pumping device. In one embodiment, the composition may be administered as part of an infusion or may be added to cells or tissues. In one embodiment, the conjugate may be administered in the form of a tablet.

In the context of the present application, the term senescence may relate to natural, premature, induced or accelerated senescence.

In one embodiment, the conjugate may comprise an amino acid, peptide, protein, lipid, sugar, polysaccharide, inorganic or organic acid attached to one of the hydroxyl groups. In another embodiment, the conjugate may comprise an aryl or alkyl group or alkaline metal attached at position $R^1$, $R^2$, $R^3$ or $R^4$. More preferably, the aryl or alkyl group or alkaline metal may be attached at position $R^1$.

In one embodiment, the composition may be pyrogen free. In one embodiment, the conjugate may be provided in the form of a free base or a pharmaceutically acceptable salt.

In one embodiment, the conjugate may comprise a pharmaceutically acceptable carrier or delivery system which may be in the form of water and oil emulsions, suspensions, colloids, microemulsions, suspensions or emulsions of vesicles, micelles, liposomes, microparticles, nanoparticles, powders or anhydrous compositions. The conjugate may also be coated or combined with a material such as a lipid or sugar, or a combination thereof. The conjugate may be linked to an amino acid, peptide, antibody or other suitable molecule to enable targeting of the conjugate to cells, tissues or organs. In one embodiment, the conjugate may be linked to a protein, amino acid, aryl group, alkyl group, fatty acid, sugar, lipid, flavonoid, sugar, salt or ester or other functional group, or an isoform thereof. In one embodiment, the conjugate may be linked to a glycine or taurine residue. Preferably, the coating or target-guiding material may dissolve to allow efficient and sufficient delivery of the conjugate to the cells, tissues or organs.

The composition may comprise at least one anti-inflammatory agent selected from *Boswellia serrata*, corosolic acid, ursolic acid, oleanolic acid, salicinol (salacia), rosmarinic acid, ruscogenins, darutoside, asiaticoside, sericoside, harpagoside, horse chestnut (escin, esculin), ginger (gingerol), turmeric extract (tetrahydrocurcuminoids), corydalis, myricetin, artichoke, alfalfa, tea, coffee and/or combinations thereof, or an antioxidant. The composition may comprise a divalent and/or a polyvalent metal ion, for example, copper, zinc, iron, selenium, vanadium or manganese.

In one embodiment, the composition may be administered in combination with an adjuvant, such as an anti-inflammatory drug, an extract or a natural agent. In another embodiment, the composition may further comprise an antioxidant, and/or inhibitor of Nuclear Factor-kappaB (NF-kappa B), or an inhibitor of an MMP, or an antibiotic or vitamin, for example, vitamin D, vitamin D3, vitamin C dehydroascorbate, vitamin B, vitamin E, or other suitable vitamin and/or co-factor.

In one embodiment, the composition may be used in combination with another therapy, including antibodies, analgesics, substances used to neutralise the acidity of saliva, chemotherapy, synergistic compounds, genes, gene products, cell therapy and/or radiation.

In one embodiment, the composition may be used for the reversal of senescence-associated degeneration of cells, including stem cells and cells of teeth and associated structures and/or tissues of the mouth.

In another embodiment, the composition may be used for maintaining or extending the viability of cells, including stem cells, before and/or after the process of transplantation of teeth and other structures and/or tissues in the mouth.

In one embodiment, the composition may be manufactured in a laboratory or on an industrial scale by solid-phase synthesis or other means, and may be purified to provide a therapeutically effective dose of the composition.

Advantageously, the composition may be used in human therapeutics and/or in veterinary practice, and is typically administered to a mammalian subject.

Advantageously, the composition may be administered with a high degree of safety.

The invention will be further described by way of example and with reference to the following figures, in which.

Figure 1:
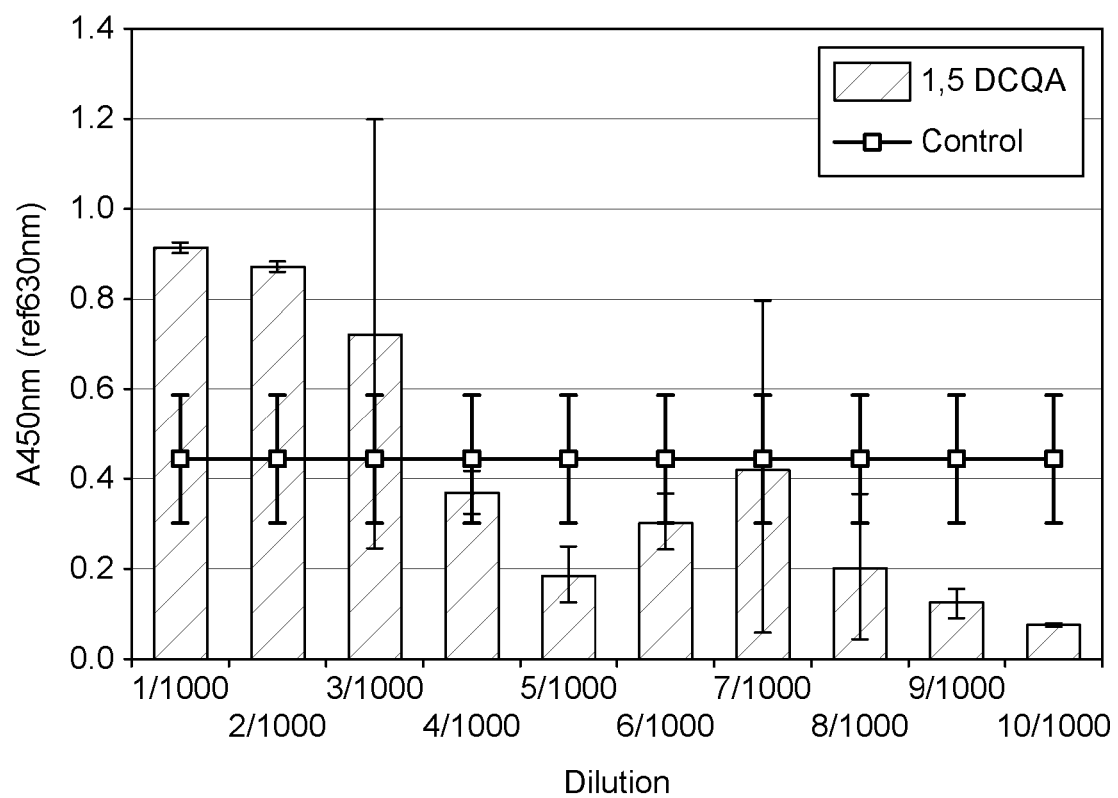
FIG. 1 shows the results of a WST-1 cell proliferation assay of 1,5-Dicaffeoylquinic Acid (1,5-DCQA)

With reference to the Figures, there is provided use of a composition for the prevention, amelioration and/or treatment of conditions, disorders and/or diseases associated with senescence and/or inflammation of the teeth and/or associated structures and tissues in the mouth, the composition comprising a conjugate of quinic acid with at least one molecule of caffeic acid, or a derivative, isomer or salt thereof.

The composition preferably comprises a dicaffeoylquinic acid and/or a tricaffeoylquinic acid, or a derivative, isomer or salt thereof. Preferably, the composition comprises a conjugate selected from 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, 4,5-dicaffeoylquinic acid, 3,4,5-tricaffeoylquinic acid, or a derivative, isomer, extract or salt thereof.

The conjugate is preferably a plant extract, and typically an artichoke extract. The composition is typically carried within a vesicle, micelle, liposome, nanoparticle or other suitable vehicle. In one embodiment, the composition may be applied directly to the mouth. In another embodiment, the composition may be provided in the form of a mouthwash, toothpaste, lotion, gel, powder, or other medium suitable for the administration of the composition to the mouth and/or may be admixed with any ingredient used in the course of dental practice.

Preferably, the composition comprises a delivery system comprising vitamins, hormones, minerals, plant extracts, anti-inflammatory agents, anti-oxidants, concentrates of plant extracts, penetration enhancers, solublizers, and/or pH adjusters.

The conjugate may be provided be in the form of a free base, or in the form of a pharmaceutically acceptable salt.

The conjugate may be administered via a pharmaceutically acceptable delivery system which may be in the form of emulsions, microemulsions, suspensions, colloids, suspensions or emulsions of vesicles, micelles, liposomes or nanoparticles, powders or by direct application.

Underpinning these properties is the observation that these compounds increase the cellular levels of sirtuin 3 (SIRT3) and decrease the level of sirtuin 2 (SIRT2). These proteins are known to regulate the processes governing cell senescence, wherein SIRT3 is associated with decreasing and SIRT2 is associated with increasing senescence. The well-known biomarker of cell senescence p16 may also be inhibited by the use of the composition (see FIG. 2).

The safety of the composition when applied to human cells is evidenced by its effect on the XRCC 5 gene (see FIG. 4), even in conditions when this gene was sub-lethally stressed with oxidant. XRCC5 is a double strand break repair gene which was unaffected under stressed conditions, indicating that the composition did not induce double strand breaks in DNA. Human lymphocyte counts after mitogen stimulation with phytoagglutinin (PHA) did not diminish significantly during experiments, further indicating the safety of the composition.

The use of the composition to inhibit key pro-senescence proteins and genes, including NF-kappaB, pro-inflammatory cytokines, p16 INK4a and sirtuin 2, together with the up regulation of sirtuin 3 may therefore offer prevention, amelioration and/or treatment of a range of conditions and diseases in which these are over expressed, including those of the mouth and other tissues and associated structures. The up regulation of sirtuin 3 by the use of the composition may not only provide a positive drive against the senescence process, but may also be able to reverse some of the cellular changes induced by the senescence process.

Preferably, the composition may be used for the prevention, amelioration and/or treatment of disorders or diseases associated with an increase in the expression of MMP genes and/or proteins. In a preferred embodiment, the composition inhibits MMPs, NF-kappa B, and/or TIMP activators. In one embodiment, the disorder or disease is associated with an increase in the expression of MMP-9 and/or MMP-2. Typically, the composition inhibits MMP-9 and/or MMP-2. MMP-9 has been found to be present at increased concentrations in the cells, tissues, in certain conditions and diseases such as caries, gum retraction and leukoplakia.

The use of the composition advantageously inhibits key pro-inflammatory proteins such as TNF-alpha and MMP-9, and may be used in the amelioration and/or treatment of diseases and disorders involving over expression of MMPs, such as chronic inflammatory disorders.

Compositions in accordance with the invention are preferably used in human therapeutics, but may also be used in veterinary practice. In the latter, the composition may be applied to a mammal, whether in the laboratory, in captivity, or in the wild, on a farm, in industry or domestic situations.

Other objectives, advantages and scope of the composition will be presented in the detailed description and will become understood by those skilled in the art, or learned by practice in its use.

Figure 8:
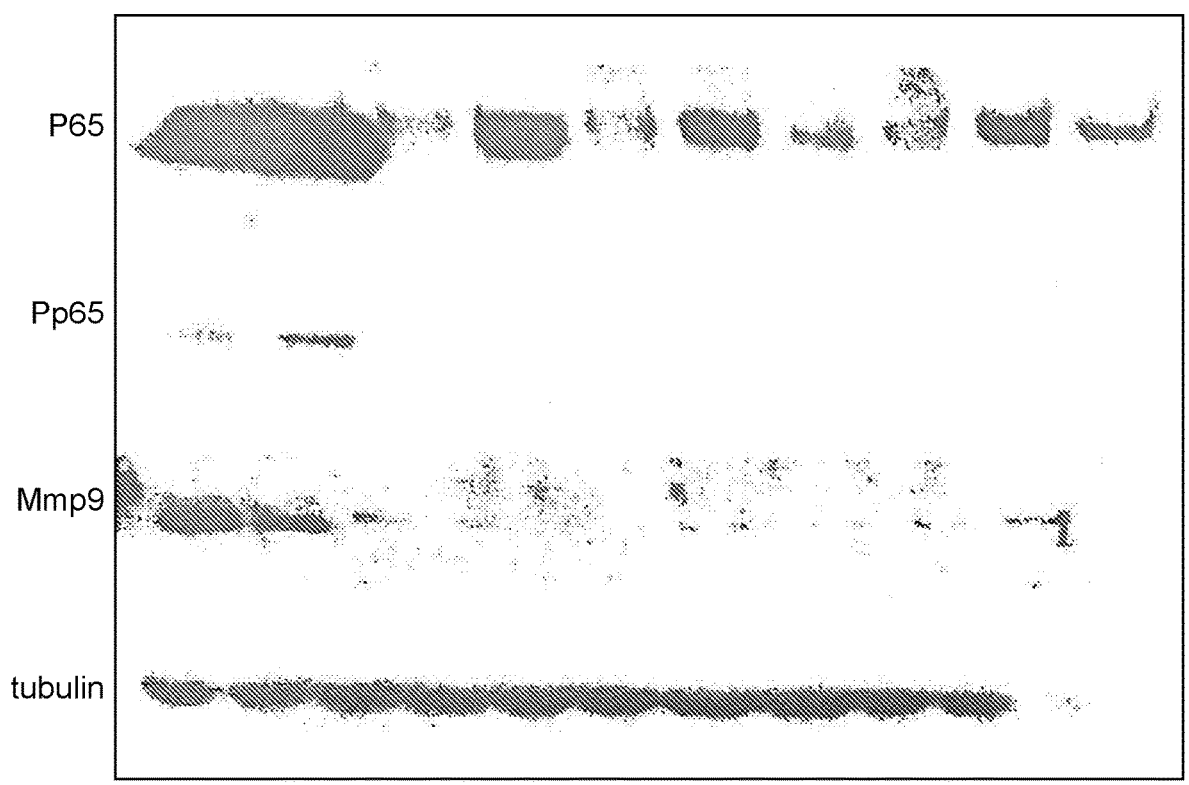
FIG. 8 shows the results of the effect of 1,4-Dicaffeoylquinic acid on p65 inhibition.

The following results relate to the analysis of senescence tests on 1,5-Dicaffeoylquinic Acid (1,5-DCQA). FIG. 8 relates to 1,4-DCQA. The experiments were conducted using human foreskin fibroblasts (HFFs).

FIG. 1 shows the results of a WST-1 Cell Proliferation Assay of 1,5-DCQA in HFFs. The WST-1 Cell Proliferation Assay provides a sensitive and accurate assay for cell proliferation and cytotoxicity (cell viability). The WST assay is based on the cleavage of the tetrazolium salt WST-1 to formazan by cellular mitochondrial dehydrogenases. Expansion in the number of viable cells results in an increase in the overall activity of the mitochondrial dehydrogenases in the sample. The augmentation in enzyme activity results in an increase in the amount of formazan dye formed. The formazan dye produced by viable cells was quantified by a multi-well spectrophotometer by measuring the absorbance of the dye solution at 440 nm. The compound provided was tested in the WST assay over a range of dilutions. The data generated indicated that 1,5-DCQA appeared to be beneficial to cell viability at 1/1000 and 2/1000 dilutions. Table 1 and FIG. 1 show the results of the WST-1 Cell Proliferation Assay. The results of the assay show the standard deviation (SD) for 1,5-DCQA and the control, and the mean values for 1,5-DCQA and the control.

TABLE 1

| Dilution | Mean 1/5-DCQA | Mean Control |
|---|---|---|
| 1/1000 | 0.916 | 0.438 |
| 2/1000 | 0.868 | 0.438 |
| 3/1000 | 0.717 | 0.438 |
| 4/1000 | 0.363 | 0.438 |
| 5/1000 | 0.178 | 0.438 |
| 6/1000 | 0.300 | 0.438 |
| 7/1000 | 0.419 | 0.438 |
| 8/1000 | 0.196 | 0.438 |
| 9/1000 | 0.115 | 0.438 |
| 10/1000 | 0.069 | 0.438 |

| Dilution | SD 1,-5-DCQA | SD Control |
|---|---|---|
| 1/1000 | 0.007 | 0.140 |
| 2/1000 | 0.011 | 0.140 |
| 3/1000 | 0.477 | 0.140 |
| 4/1000 | 0.047 | 0.140 |
| 5/1000 | 0.064 | 0.140 |
| 6/1000 | 0.059 | 0.140 |
| 7/1000 | 0.370 | 0.140 |
| 8/1000 | 0.161 | 0.140 |
| 9/1000 | 0.030 | 0.140 |
| 10/1000 | 0.005 | 0.140 |

In the following experiments, HFFs were challenged for a period of two hours with 150 μM hydrogen peroxide ($H_2O_2$), to stimulate premature senescence in the presence and absence of 1,5-DCQA (1/1000 dilution), and subsequently assayed by Taqman Real Time-PCR for the expression of key senescence associated genes.

Figure 2:
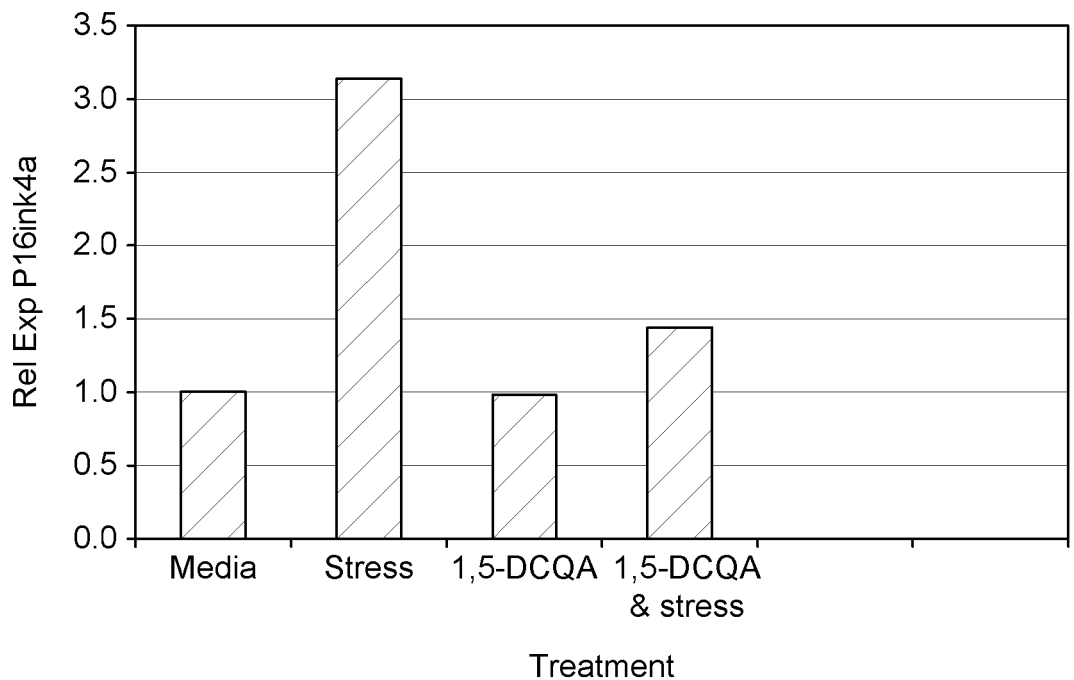
FIG. 2 shows the results of expression of p16 in cells following incubation with 1,5-DCQA.

FIG. 2 shows the relative expression of p16 in HFFs incubated with 1,5-DCQA with and without stress-induced premature senescence with 150 μM $H_2O_2$. The results indicate that 1,5-DCQA had no stress effect on untreated cells (i.e. no $H_2O_2$) and gave excellent protection from oxidant challenge, as no gross increase in expression was observed following insult.

Figure 3:
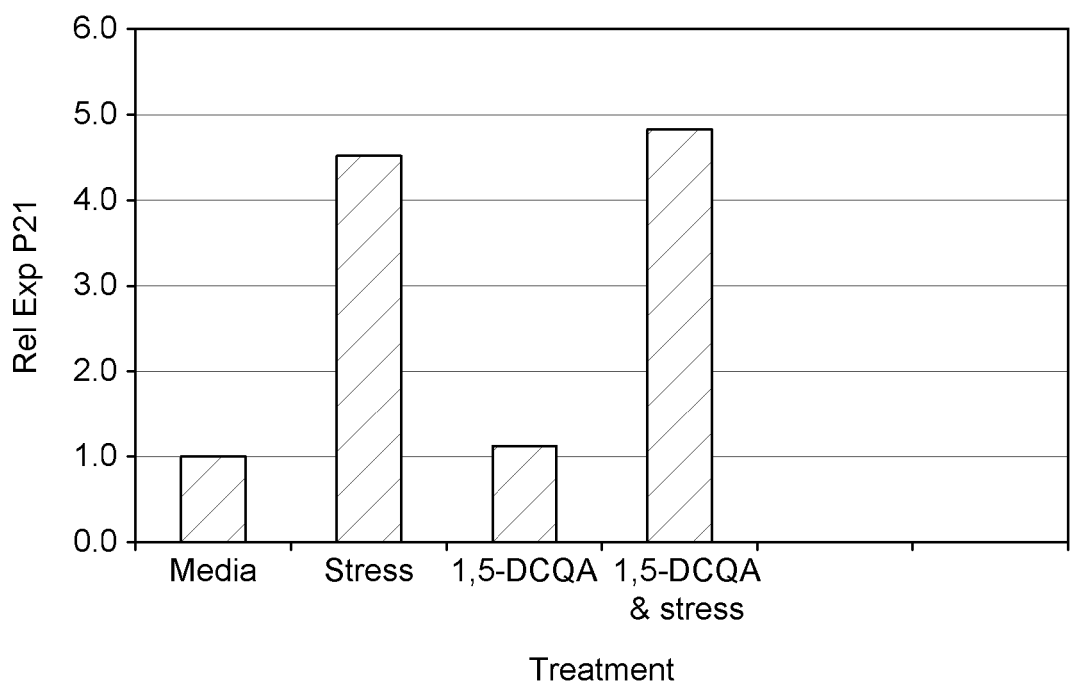
FIG. 3 shows the results of expression of p21 in cells incubated with 1,5-DCQA.

FIG. 3 shows the relative expression of p21 in HFFs incubated with 1,5-DCQA with and without stress-induced premature senescence with 150 μM $H_2O_2$. As the inhibition mediated with 1,5-DCQA is known to occur downstream of the p21 gene, the expression levels are substantially unchanged following stress.

Figure 4:
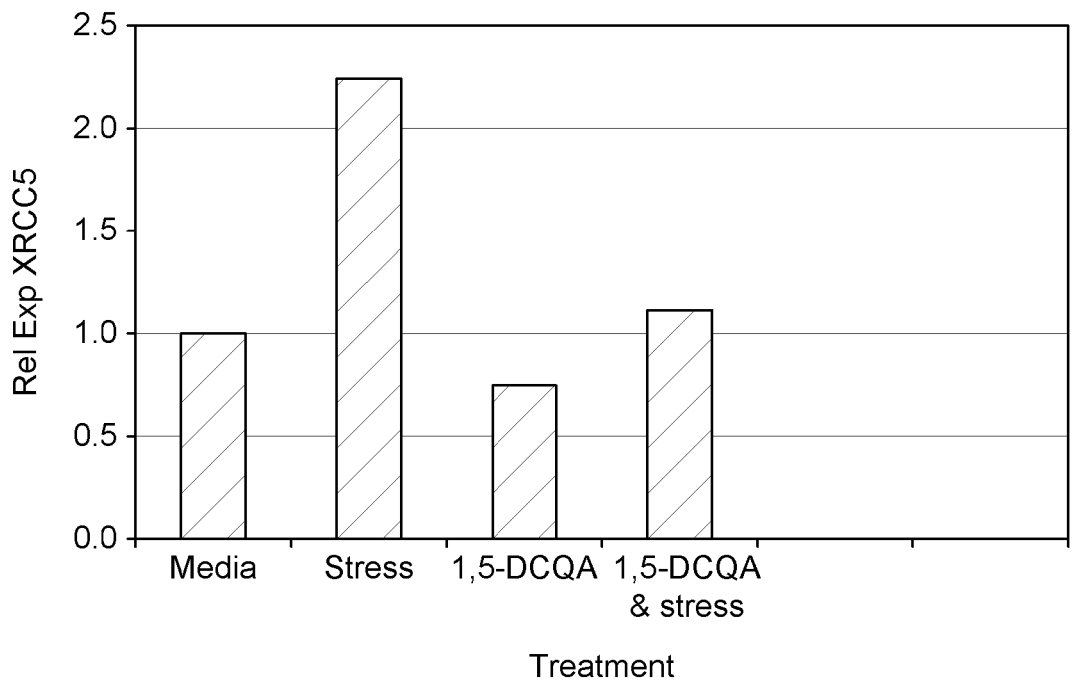
FIG. 4 shows the results of expression of XRCC5 in cells following incubation with 1,5-DCQA.

FIG. 4 shows the relative expression of XRCC5 in HFFs with 1,5-DCQA with and without stress-induced premature senescence with 150 μM $H_2O_2$. XRCC5 is a double strand break repair protein. The substantially unaltered expression of XRCC5, in comparison with the control data set, indicates that the compound does not induce DNA breaks per se and mitigates against the effects of oxidant challenge.

Figure 5:
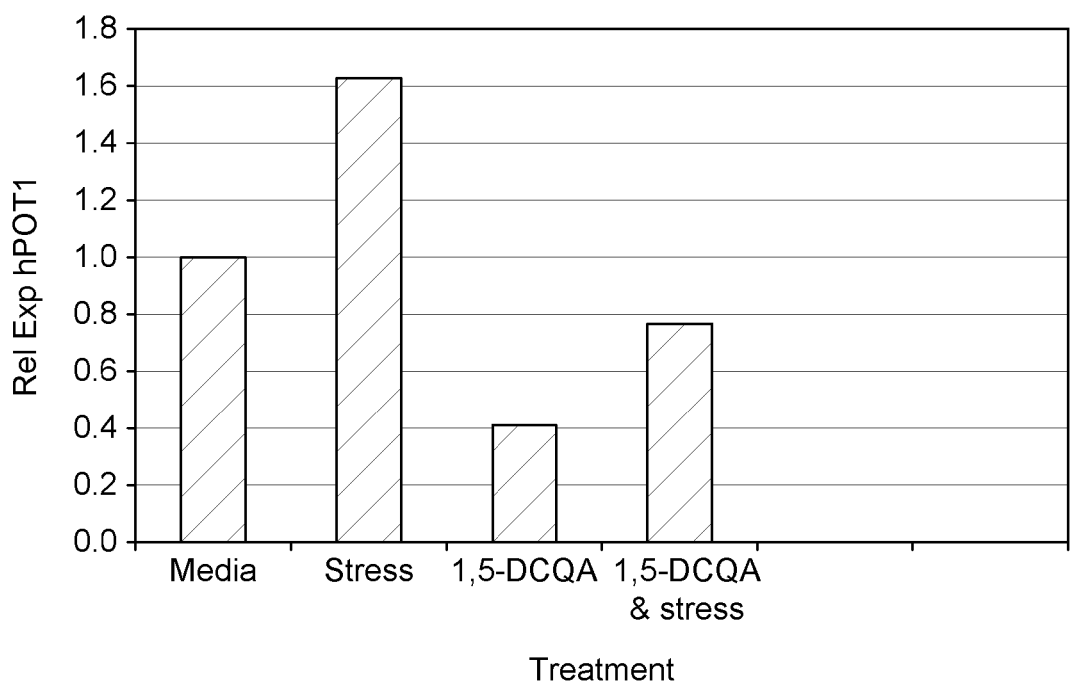
FIG. 5 shows the results of expression of hPOT1 in cells following incubation with 1,5-DCQA.

These findings are supported by an analysis of the Protection of Telomeres gene (POT 1). FIG. 5 shows the relative expression of hPOT1 in HFFs incubated with 1,5-DCQA with and without stress-induced premature senescence with 150 μM $H_2O_2$. The results indicate a protective effect induced the compound against oxidant challenge, consistent with the previous data sets.

Figure 6:
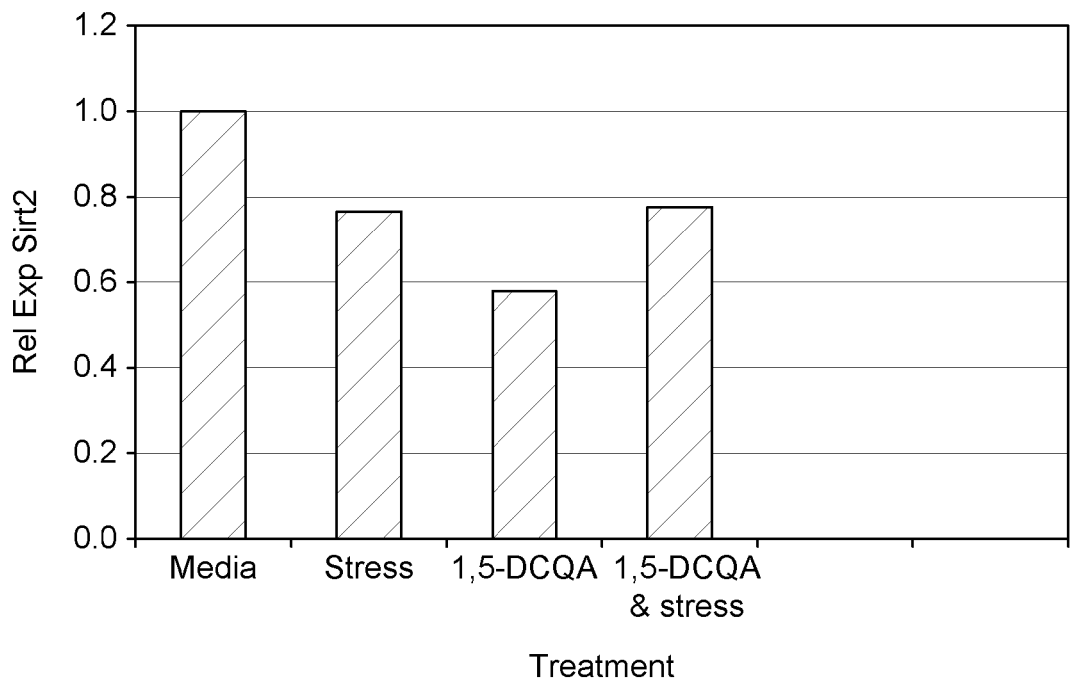
FIG. 6 shows the relative expression levels of sirtuin 2 in cells following incubation with 1,5-DCQA.
Figure 7:
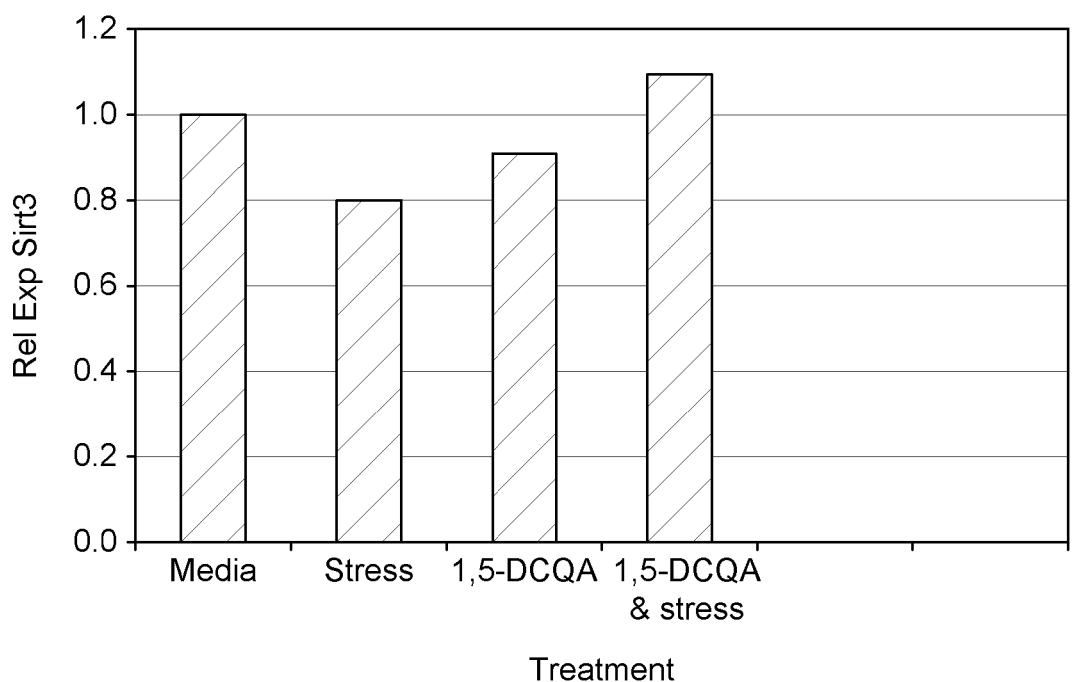
FIG. 7 shows the relative expression levels of sirtuin 3 in cells following incubation with 1,5-DCQA.

FIG. 6 shows the relative expression of Sirtuin 2 (SIRT2) in HFFs incubated with 1,5-DCQA with and without stress-induced premature senescence with 150 μM $H_2O_2$. FIG. 7 shows the relative expression of Sirtuin 3 (SIRT3) in HFFs incubated with 1,5-DCQA with and without stress-induced premature senescence with 150 μM $H_2O_2$. These genes are involved in cell cycle regulation and mitochondrial stress responses. Challenge with a near lethal level of oxidant stress typically induces an increase in SIRT2 and decrease in SIRT3 expression. The compound 1,5-DCQA induced a significant decrease in SIRT2 expression without stress. This is indicative of each having a potential for stimulating cell proliferation in the absence of oxidant challenge. 1,5-DCQA induced an increase in SIRT3 expression following oxidant challenge, indicating that it has a superior protective effect on the cells.

Table 2 below shows a summary of the data obtained to generate the results shown in FIGS. 2 to 7.

TABLE 2

| Expression of P16 | | | | |
|---|---|---|---|---|
| | HPRT | P16 | dCt | ddCt (1.275) | Relative Expression |
| media | 27.90031 | 29.17546 | 1.275 | 0.000 | 1.000 |
| stress | 28.55117 | 28.17046 | −0.381 | −1.656 | 3.151 |
| 1,5-DCQA | 26.33103 | 27.65584 | 1.325 | 0.050 | 0.966 |
| 1,5-DCQA & stress | 27.33624 | 28.09219 | 0.756 | −0.519 | 1.433 |

| Expression of P21 | | | | |
|---|---|---|---|---|
| | HPRT | P21 | dCt | ddCt (−3.761) | Relative Expression |
| media | 27.90031 | 24.13934 | −3.761 | 0.000 | 1.000 |
| stress | 28.55117 | 22.6142 | −5.937 | −2.176 | 4.519 |
| 1,5-DCQA | 26.33103 | 22.40333 | −3.928 | −0.167 | 1.122 |
| 1,5-DCQA & stress | 27.33624 | 21.31201 | −6.024 | −2.263 | 4.801 |

| Expression of SIRT2 | | | | |
|---|---|---|---|---|
| | HPRT | SIRT2 | dCt | ddCt (−0.016) | Relative Expression |
| media | 27.90031 | 27.91659 | 0.016 | 0.000 | 1.000 |
| stress | 28.55117 | 28.96023 | 0.409 | 0.393 | 0.762 |
| 1,5-DCQA | 26.33103 | 27.16427 | 0.833 | 0.817 | 0.568 |
| 1,5-DCQA & stress | 27.33624 | 27.72334 | 0.387 | 0.371 | 0.773 |

| Expression of SIRT3 | | | | |
|---|---|---|---|---|
| | HPRT | SIRT3 | dCt | ddCt (−2.079) | Relative Expression |
| media | 27.90031 | 29.97938 | 2.079 | 0.000 | 1.000 |
| stress | 28.55117 | 30.96285 | 2.412 | 0.333 | 0.794 |
| 1,5-DCQA | 26.33103 | 28.55774 | 2.227 | 0.148 | 0.903 |
| 1,5-DCQA & stress | 27.33624 | 29.29568 | 1.959 | −0.120 | 1.086 |

| Expression of XRCC5 | | | | |
|---|---|---|---|---|
| | HPRT | XRCC5 | dCt | ddCt (−−1.292) | Relative Expression |
| media | 27.90031 | 26.60795 | −1.292 | 0.000 | 1.000 |
| stress | 28.55117 | 26.09751 | −2.454 | −1.162 | 2.237 |

TABLE 2-continued

| 1,5-DCQA | 26.33103 | 25.48349 | −0.848 | 0.444 | 0.735 |
| 1,5-DCQA & stress | 27.33624 | 25.90307 | −1.433 | −0.141 | 1.103 |

Expression of hPOT1

|  | HPRT | HPOT1 | dct | ddct (−1.835) | Relative Expression |
| --- | --- | --- | --- | --- | --- |
| media | 27.90031 | 29.73482 | 1.835 | 0.000 | 1.000 |
| stress | 28.55117 | 29.6853 | 1.134 | −0.701 | 1.625 |
| 1,5-DCQA | 26.33103 | 29.47246 | 3.141 | 1.306 | 0.404 |
| 1,5-DCQA & stress | 27.33624 | 29.5758 | 2.240 | 0.405 | 0.755 |

The results shown in Table 2 and FIGS. 2 to 7 were generated using the polymerase chain reaction (PCR), wherein the dCt and ddCT values are results used in statistical analysis. The abbreviation dCt relates to "delta cycle threshold" and the abbreviation ddCt relates to "delta delta cycle threshold". In these experiments, HPRT (hypoxanthine phosphoribosyltransferase, a protein from the HPRT-1 gene) was used as a control.

The results indicate that 1,5-DCQA has desirable properties as a protective agent during cell stress. This compound therefore protects mitochondria from stress, as determined by the level of SIRT 3 expression. The mode of action of this compound is understood to be downstream of p21 and appears to influence telomere biology in a positive fashion following oxidative insult. The results indicate that in normal fibroblasts, the compound (1,5-DCQA) down regulates SIRT2 expression by approximately 52%, but up regulates SIRT3 expression by approximately 36% in senescent fibroblasts. Thus, the results shown in Table 2 and in FIGS. 2 to 7 illustrate the beneficial properties of the composition. Advantageously, use of the composition does not completely inhibit the expression of SIRT2, since some SIRT2 expression is required for 'housekeeping' activities within the cell.

FIG. 8 shows the results of a Western blot which was performed on 50 μg of extracts from LNCaP cells and probed for p65, Pp65 (ser 536 of NFkappaB) and MMP-9 expression. Lanes 1 and 2 of the Western blot show the expression levels Hela control lysates comprising TNF-alpha (TNFα), in stimulated and unstimulated conditions. Lanes 3 and 4 show the results of LNCaP cell extracts, in stimulated and unstimulated conditions. In this case, the vehicle used is ethanol. Lanes 5 to 10 show the results of LNCaP cell extracts incubated for 24 hours in 0.1, 1, 3, 10, 30 and 100 μM of 1,4-DCQA, respectively. Tubulin (50 kD) was used as a loading control. P65 and Pp65 are known to be part of the NF-kappa B gene. The results show that 1,4-DCQA does not inhibit the expression of p65, but does inhibit the phosphorylation of p65 subunit of NFkappaB. The inhibition of MMP-9 is also clearly demonstrated at 0.1 μM to 100 μM.

Figure 9:
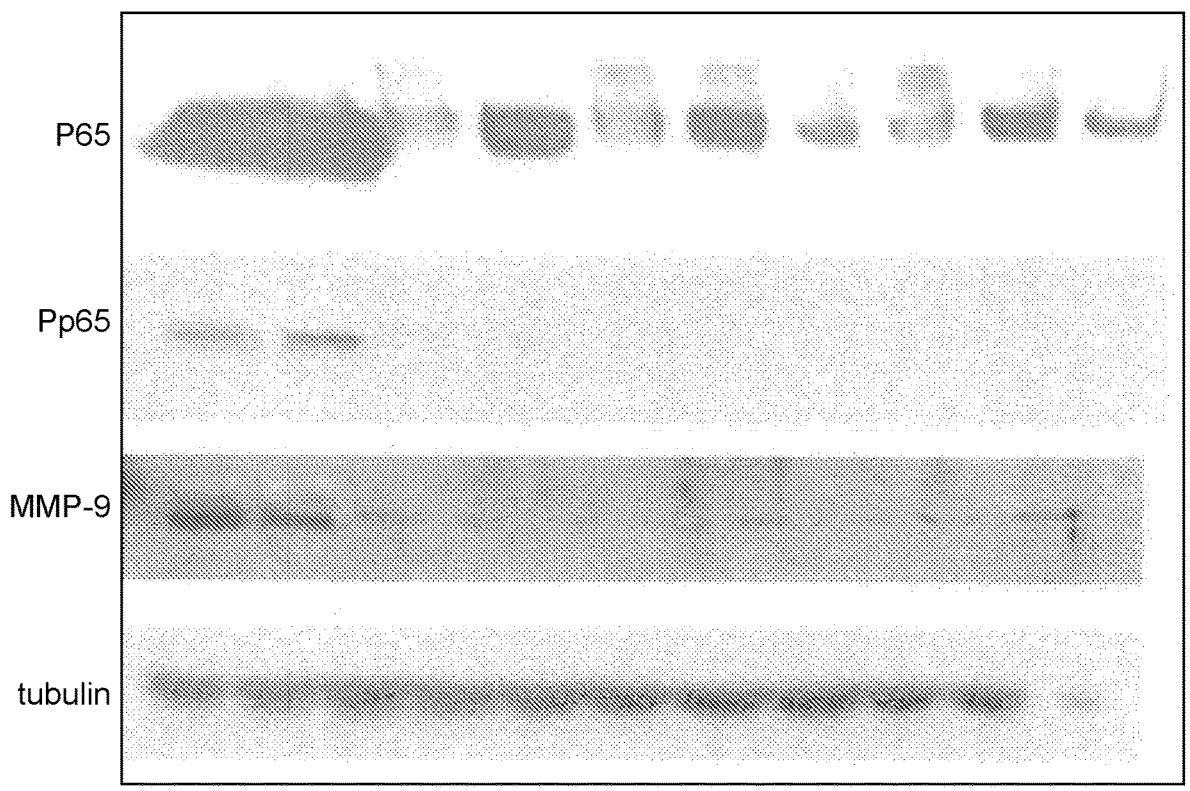
FIG. 9 shows the results of the effect of 1,5-Dicaffeoylquinic acid on p65 inhibition.

FIG. 9 shows the results of a Western Blot illustrating the effect of 1,5-DCQA on p65 inhibition. The Western Blot was performed on 50 μg of extracts from LNCaP cells and probed for p65, Pp65 (ser 536 of NFkappaB) and MMP-9 expression. Lanes 1 and 2 of the Western blot show the expression levels Hela control lysates comprising TNF-alpha (TNFα), in stimulated and unstimulated conditions. Lanes 3 and 4 show the results of LNCaP cell extracts, in stimulated and unstimulated conditions. In this case, the vehicle used is ethanol. Lanes 5 to 10 show the results of LNCaP cell extracts incubated for 24 hours in 0.1, 1, 3, 10, 30, 100 μM of 1,5-DCQA, respectively. Tubulin (50 kD) was used as a loading control. The results show that 1,5-DCQA does not inhibit the expression of p65, but does inhibit the phosphorylation of p65 subunit of NFkappaB. The inhibition of MMP-9 is also clearly demonstrated at 0.1 μM to 100 μM.

These results clearly show that 1,4-DCQA and 1,5-DCQA inhibit Nuclear factor kappa B by preventing the phosphorylation of serine 536 in its p65 subunit. This provides a mechanism for the downstream actions on cytokines and a platform for the use of the composition in the therapeutic areas described.

The invention claimed is:

1. A method for the amelioration or treatment of conditions, disorders or diseases associated with senescence of the teeth, associated structures or tissues in the mouth; or inflammation of the teeth, associated structures or tissues in the mouth, the method comprising administering a composition comprising a conjugate of (a) quinic acid with (b) at least one molecule of caffeic acid, or a derivative, isomer or salt thereof.

2. The method of claim 1, wherein the composition comprises an ester of caffeic acid and quinic acid, a dicaffeoylquinic acid, or a tricaffeoylquinic acid, or a derivative, isomer or salt thereof.

3. The method of claim 1, wherein the composition comprises 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, 4,5- dicaffeoylquinic acid, or 3,4,5-tricaffeoylquinic acid, or a derivative, isomer or salt thereof.

4. The method of claim 1, wherein the composition inhibits one or more of a matrix metalloproteinase (MMP), MMP-9, MMP-2, nuclear factor kappa B, a cytokine, or a tissue inhibitor of matrix metalloproteinase (TIMP) activator.

5. The method of claim 1, wherein the method results in (a) an increase in the expression of one or more matrix metalloproteinase (MMP) genes or proteins and (b) the control of the concentration of MMPs in saliva to increase the extracellular matrix cohesion of the teeth and associated structures and tissues of the mouth.

6. The method of claim 1, wherein the composition (a) activates the expression of the sirtuin 3 gene to enhance the production of the sirtuin 3 protein, (b) inhibits the expression of the sirtuin 2 gene, (c) inhibits the production of the sirtuin 2 protein, or (d) a combination thereof.

7. The method of claim 1, wherein the method comprises (a) amelioration or treatment of demineralization of the enamel or dentine of the teeth and associated structures in the mouth and (b) stimulation or promotion of remineralization of teeth or associated structures in the mouth.

8. The method of claim 1, wherein the method comprises stimulation or promotion of remineralization of teeth or associated structures in the mouth following demineralization of teeth.

9. The method of claim 1, wherein the method comprises the amelioration or treatment of leukoplakia.

10. The method of claim 1, wherein the method comprises the amelioration or treatment of chronic inflammatory disease of the teeth and associated structures of the mouth or dental caries.

11. The method of claim 1, wherein the method comprises the amelioration or treatment of conditions of the teeth or associated structures in the mouth associated with senescence.

12. The method of claim 1, wherein the method comprises the amelioration or treatment of tissue shrinkage or contraction which may occur in senescence following application of a dental implant or prosthesis in the mouth.

13. The method of claim 1, wherein the composition is incorporated into a coating or other material used in a dental implant or prosthesis.

14. The method of claim 1, wherein the composition is incorporated into teeth whitening agents and the method comprises the amelioration or treatment of conditions affected by free radicals, hydrogen peroxide or associated derivatives which may be generated by the use of teeth whitening agents.

15. The method of claim 1, wherein the conjugate is extracted from a natural source, is a plant extract, is an artichoke extract, is synthesized, or is engineered from plants, bacteria, fungi, mold, algae or another suitable source.

16. The method of claim 1, wherein the composition comprises at least one acceptable carrier and the conjugate is carried within dental inserts, vesicles, micelles, liposomes, nanoparticles, or other suitable vehicles.

17. The method of claim 1, wherein the composition is directly applied to the teeth or associated structures in the mouth.

18. The method of claim 1, wherein the composition is directly applied to the teeth or associated structures in the mouth by a dental practitioner during a surgical procedure, or by injection, or wherein the composition is applied in the form of a mouthwash, paste, toothpaste, lotion, gel, powder or other suitable medium.

19. The method of claim 1, wherein the composition comprises a free base form of the conjugate or a pharmaceutically acceptable salt of the conjugate.

20. The method of claim 1, wherein the composition is used in combination with one or more other therapies comprising antibodies, analgesics, substances used to neutralize the acidity of saliva, chemotherapy, synergistic compounds, genes, gene products, cell therapy, radiation, or other suitable therapies.

\* \* \* \* \*